United States Patent [19]

Blum

[11] Patent Number: 5,246,738
[45] Date of Patent: Sep. 21, 1993

[54] HYDRIDOSILOXANES AS PRECURSORS TO CERAMIC PRODUCTS

[75] Inventor: Yigal Blum, San Jose, Calif.

[73] Assignee: SRI International, Menlo Park, Calif.

[21] Appl. No.: 870,286

[22] Filed: Apr. 17, 1992

Related U.S. Application Data

[63] Continuation of Ser. No. 341,722, Apr. 21, 1989, Pat. No. 5,128,494, which is a continuation-in-part of Ser. No. 12,874, Dec. 1, 1986, Pat. No. 5,008,422, which is a continuation-in-part of Ser. No. 908,685, Mar. 4, 1986, Pat. No. 4,788,309, which is a continuation-in-part of Ser. No. 727,415, Apr. 26, 1985, Pat. No. 4,612,383.

[51] Int. Cl.$^5$ .............................................. B05D 3/02
[52] U.S. Cl. ...................................... 427/387; 501/88; 501/97; 556/410; 556/412; 427/228; 427/397.7; 427/383.1; 427/383.7; 427/113; 427/162; 427/199; 427/58; 427/126.1; 427/126.2; 427/126.3; 427/126.5; 427/126.6

[58] Field of Search ................... 561/88, 97; 427/228, 427/397.7, 383.1, 383.7, 58, 113, 162, 199, 383.5, 126.1, 126.2, 126.3, 126.15, 126.6, 387; 556/410, 412

[56] References Cited

U.S. PATENT DOCUMENTS

| | | | |
|---|---|---|---|
| 4,482,669 | 11/1984 | Seyferth et al. | 556/412 X |
| 4,482,689 | 11/1984 | Haluska et al. | 556/412 X |
| 4,659,850 | 4/1987 | Arai et al. | 556/412 X |
| 4,720,532 | 1/1988 | Seyferth et al. | 501/97 X |
| 4,767,876 | 8/1988 | Seyferth et al. | 556/410 |

Primary Examiner—Paul F. Shaver
Attorney, Agent, or Firm—Dianne E. Reed

[57] ABSTRACT

A method is provided for preparing preceramic polymers and and silicious ceramic materials which derive therefrom. The preceramic polymers are polysiloxanes which are synthesized by catalytically activating Si—H bonds in a hydridosiloxane starting material and replacing the activated hydrogen atoms with non-hydrogen substituents. These preceramic polysiloxanes are pyrolyzed in a selected atmosphere to give the desired ceramic product. Ceramic products which may be prepared by this technique include silica, silicon oxynitride, silicon carbide, and metal silicates.

32 Claims, No Drawings

HYDRIDOSILOXANES AS PRECURSORS TO CERAMIC PRODUCTS

This application is a continuation of application Ser. No. 341,722, filed Apr. 21, 1989, now U.S. Pat. No. 5,128,494, which is a continuation-in-part of Ser. No. 012,874, filed Dec. 1, 1986, now U.S. Pat. No. 5,008,422, which is a continuation-in-part of Ser. No. 908,685, filed Mar. 4, 1986, now U.S. Pat. No. 4,788,309, which is a continuation-in-part of Ser. No. 727,415, filed May, 26, 1985, now U.S. Pat. No. 4,612,383.

TECHNICAL FIELD

This invention relates generally to preceramic polymers and preparation of ceramic products therefrom. More particularly, the invention relates to the use of hydridosiloxanes as precursors to ceramic products such as silica, silicon oxynitride, silicon carbide, and metal silicates.

BACKGROUND OF THE INVENTION

The invention relates primarily to: (1) the preparation of polymers that are useful as precursors to ceramic materials (i.e., which serve as "preceramic" polymers); and (2) catalytic activation of Si-H bonds. The invention also concerns, in one embodiment, the use of sol-gel processing techniques.

The sol-gel process is an important route for advanced metal-oxide glasses and ceramics. The method is currently used or of potential for protective, optical and electronic coatings, optical fiber preforms, nonlinear optical devices, dielectrics or superconductors, display materials, and structures. The sol-gel technique provides a relatively low temperature, controlled method of producing a large variety of shapes such as monodispersed particles, uniform coatings, fibers, dense or porous articles, and mixed metal oxides having controlled stoichiometry and purity at the molecular level.

The sol-gel process has been based mostly on the same group of starting materials, the metal alkoxides, carboxylates and diketonates. These precursors are hydrolyzed, then condensed in the presence of an alcohol/water solution to form a gel which is dried and fired to give the final product. Chemical control of product formation is manipulated by temperature, type of catalyst and pH as well as by the type and ratio of reactants in solution. See, e.g., C. J. Brinker et al., in "Ultrastructure Processing of Ceramics, Glasses and Composites I" (1984), at pp. 43 et seq.

Thus, the reaction procedure controls to a large extent the morphology of the final gel, and, therefore, the final ceramic microstructure as well. Low water content and/or acidic conditions will give spinnable gels because the precursor polymer will, as noted above, be substantially linear. Higher water content will give slightly crosslinked, coatable gels, while a very high water content and/or basic conditions will give highly crosslinked gel products that are useful in casting processes and for powder formation. See B. J. J. Zelinski et al., *J. Phys. Chem. Solids* 45:1069 (1984), and L. C. Klien et al., *Ann. Rev. Mat. Sci.* 15:227 (1985).

It has recently been suggested that alkoxidesiloxane oligomers may serve as molecular building blocks for unique ceramic silica structures (V. W. Day et al., *J. Am. Chem. Soc.* 107:8264 (1985)). A rigid cubic alkoxysesquisiloxane, $[Si_8O_{12}](OCH_3)_8$, offers the possibility of generating porous materials, yet rigid due to the molecular block structure.

As noted above, the invention also relates to preparation of preceramic polymers, i.e., polymers which may be converted upon pyrolysis to ceramic products. The present invention provides preceramic siloxane polymers which are useful for preparing a wide variety of silicious ceramic materials and articles, e.g., articles such as fibers, films, shaped products, and the like, comprising materials such as silica, silicon oxynitride, silicon carbide, or metal silicate.

The preceramic polymers, or "ceramic precursors", of the invention are prepared by catalytic activation of Si—H bonds. To date, catalytic activation of Si—H bonds has mainly been used for hydrosilylation reactions of unsaturated compounds, as illustrated by reactions (1) and (2):

$$R_3Si-H + M \longrightarrow R_3Si-M-H \qquad (1)$$

$$R_3Si-M-H + R_2C=X \longrightarrow R_2CH-XSiR_3 + M \qquad (2)$$

$(X = O, CR_2)$

Over the past 25 years, numerous homogeneous and heterogeneous catalysts have been found which promote these reactions. See, e.g., J. L. Speier et al., *J. Am. Chem. Soc.* 79:974 (1957). Typical applications of these reactions have been in organic synthesis or in the crosslinking of silicon rubbers (J. P. Collman et al., in "Principles and Applications of Organotransition Metal Chemistry", pp. 384-392, University Science Books, 1980). Only recently have such reactions been found useful in another application, crosslinking of preceramic polymers, as described in co-pending, commonly assigned application Ser. No. 012,874, the disclosure of which is hereby incorporated by reference in its entirety.

Related reactions involving substitution at an Si—H bond have been used to form compounds containing Si—Y groups wherein Y is, for example, halogen, alkoxy, or substituted or unsubstituted amino:

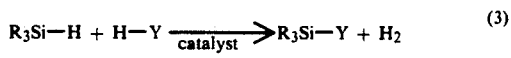
$$R_3Si-H + H-Y \xrightarrow{\text{catalyst}} R_3Si-Y + H_2 \qquad (3)$$

L. H. Sommer et al., *J. Org. Chem.* 32:4270 (1967). Only mono- and di-substituted aminosilanes, halosilanes and alkoxysilanes have been synthesized by this method. Surprisingly, there have been virtually no attempts to enlarge the potential capability of reaction (3). For example, the inventors herein are unaware of any work involving reaction of compounds containing multiple Si—H bonds with water to form oligomeric or polymeric siloxane products.

Investigators at SRI, the assignee of the present application, have recently discovered that catalytic activation of Si—H bonds is extremely useful in the synthesis of polysilazane ceramic precursors, according to reaction (4):

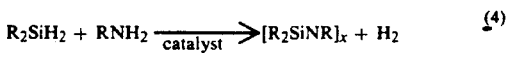
$$R_2SiH_2 + RNH_2 \xrightarrow{\text{catalyst}} [R_2SiNR]_x + H_2 \qquad (4)$$

$(R = H, \text{alkyl})$

To date, however, efforts have not been focused on enlarging the scope of the analogous reaction in the presence of water, i.e., instead of using ammonia or monoalkylamines. Preliminary research indicates that similar reactions (as illustrated by reactions (5) and (6)) will occur in the presence of water, to produce monomeric, oligomeric or polymeric siloxanes, at room temperature, or lower:

$$R_3SiH + H_2O \xrightarrow[Ru_3(CO)_{12}]{30°\,C.} R_3SiOH + R_3SiOSiR_3 + H_2 \quad (5)$$

$$R_2SiH_2 + H_2O \xrightarrow[Ru_3(CO)_{12}]{30°\,C.} [R_2SiO]_x + H_2 \quad (6)$$

The present invention is directed to a new approach to polymer processing, and involves combining the fields of research summarized hereinabove: (a) preparation of preceramic polymers useful in making ceramic materials; and (b) reaction of hydridosiloxane compounds by catalytic activation of the Si—H bonds contained therein. In a preferred embodiment, the invention also involves the use of (c) sol-gel processing techniques. Gels or preceramic polymers produced using the present method are highly "processable" and, upon pyrolysis, give the desired ceramic material in relatively high yield.

SUMMARY OF THE INVENTION

Accordingly, it is a primary object of the invention to use catalytic Si—H bond activation to produce precursors to ceramic products.

It is another object of the invention to use catalytic Si—H bond activation, in conjunction with sol-gel processing techniques, to produce ceramic precursors.

It is still another object of the invention to use catalytic Si—H bond activation to provide preceramic polysiloxanes in which hydrogen atoms in the starting material have been replaced with non-hydrogen substituents.

It is yet another object of the invention to provide a method of making preceramic polymers in which catalytically activated Si—H bonds in the hydridosiloxane starting material are replaced with Si—C, Si—N, Si—O, Si—Metal, or other linkages.

It is a further object of the invention to provide a method of making silicious ceramic products by pyrolyzing preceramic polymers synthesized via catalytic Si—H bond activation of hydrosiloxane starting materials.

It is still a further object of the invention to provide a method of making silica, silicon oxynitride, silicon carbide, and/or metal silicates by pyrolyzing various preceramic polymers as described herein.

Additional objects, advantages and novel features of the invention will be set forth in part in the description which follows, and in part will become apparent to those skilled in the art upon examination of the following, or may be learned by practice of the invention.

In one aspect of the invention, a method is provided for preparing a ceramic precursor, which comprises: (a) providing a hydridosiloxane polymer containing one or more Si—H bonds per mer unit; and (b) reacting said hydridosiloxane polymer with a hydroxyl-containing compound R'—OH, wherein R' is hydrogen, $C_1$-$C_{10}$ alkyl, or aryl of 1-2 rings (and may be substituted with one or more substituents which do not significantly hinder the reaction), in an inert atmosphere in the presence of a catalyst effective to activate Si—H bonds, to give a ceramic precursor in which hydrogen atoms have been replaced by —OR' moieties.

In other aspects of the invention, ceramic precursors are provided using a similar method, i.e., one which involves catalytic activation of Si—H bonds in a hydridosiloxane starting material, but which provides preceramic polysiloxanes in which the "activated" hydrogen atoms have been replaced with non-hydrogen, non-alkoxy substituents, e.g., nitrogen-containing, carbon-containing, or organometallic groups.

In still other aspects of the invention, silicious ceramic materials are prepared by: (1) catalytic activation of Si—H bonds in a hydridosiloxane starting material; (2) replacement of the activated hydrogen atoms by non-hydrogen substituents; and (3) pyrolysis at a selected temperature and in a selected atmosphere, to give the desired ceramic product. Depending on the pyrolysis temperature, the particular polysiloxane preceramic, and on the pyrolysis atmosphere, ceramic materials may be provided which comprise silica, silicon oxynitride, silicon carbide, metal silicates, or mixtures thereof.

In still further aspects of the invention, the hydridosiloxane starting material of the aforementioned processes is treated with water in the presence of an acid or base catalyst after an initial catalytic Si—H bond activation reaction which introduces pendant alkoxy groups. Such a step is in conformance with standard sol-gel processing techniques, and extends the degree of polymerization in or crosslinks the product. Typically, this step provides a polymeric gel.

DETAILED DESCRIPTION OF THE INVENTION

A. Definitions.

"Hydridosiloxanes" as used herein are compounds which contain one or more silicon-hydrogen bonds and one or more silicon-oxygen bonds. The term is intended to include oligomeric, cyclomeric, polymeric and copolymeric hydridosiloxanes.

The term "polymer" is intended to include both oligomeric and polymeric species, i.e., compounds which include two or more monomeric or cyclomeric hydridosiloxane units.

The "ceramic yield" of a compound upon pyrolysis indicates the ratio of the weight of the ceramic product after pyrolysis to the weight of the compound before pyrolysis.

A "lower alkyl" or "lower alkoxy" group is an alkyl or alkoxy group, respectively, having 1-6 carbon atoms, more typically 1-4 carbon atoms, therein.

"Silyl" as used herein is an

—$SiX_2$— or —$SiX_3$ moiety wherein X is hydrogen, lower alkyl, lower alkenyl or amino, unsubstituted or substituted with 1 or 2 lower alkyl or lower alkenyl groups. The "silyl" moiety may be part of a silicon-containing oligomer, cyclomer or polymer.

Hydridosiloxane "coupling agents" as used herein are intended to include any chemical reagent which is capable of bridging two hydridosiloxane units. The coupling agent typically has the formula HZH, wherein Z is oxygen, sulfur, phosphoro, amino (unsubstituted or substituted with one or more lower alkyl or silyl groups), —O—, —O—Y—O, —NX—NX—, or —NX—Y—NX—, where Y is a linking group, typically lower alkyl or silyl, and X is typically lower alkyl, silyl, or hydrogen —Z— bridges between silicon atoms of two hydridosiloxane monomeric or cyclomeric units.

B. Preparation of Ceramic Precursors

B.1. Overview

The method of the present invention involves preparation of polysiloxane ceramic precursors by catalytic Si—H bond activation of a hydridosiloxane starting material. While a number of different types of reactions and products are encompassed by the present method, each reaction involves catalytic activation of Si—H bonds in the selected hydridosiloxane material, and replacement of the activated hydrogen atoms therein.

Table 1 illustrates the various pathways and products of the invention:

TABLE 1

Starting material: Polymer containing the structure $[RSiHO]_n$

| | | Pathway | Primary Product |
|---|---|---|---|
| I. | | Pyrolyze directly | $SiO_2/SiC/C$, $Si_2ON_2$ (depending on R, temperature and pyrolysis atmosphere) |
| II. | A. | Substitute with alkoxy groups OR': react with R'OH | $[RSiHO]_l[RSiO]_m$<br>       |<br>      OR' |
| | B. | Sol-gel: prepare by catalytically reacting product of II.A. with water | $[RSiHO]_l[RSiO]_m$<br>       |<br>      O<br>      |<br>$[RSiHO]_l[RSiO]_m$ |
| | C. | Pyrolyze product of II.A. or II.B. | |
| | | 1. Under inert atmosphere | $SiO_2/SiC/C$ |
| | | 2. Under reactive amine atmosphere | $Si_2ON_2/SiO_2$ |
| | | 3. Under $O_2$ | $SiO_2$ |
| III. | A. | Sol-gel: prepare by catalytically reacting with water | $[RSiHO]_l[RSiO]_m$<br>       |<br>      OH |
| | B. | Pyrolyze product of III.A. directly | |
| | | 1. Under inert atmosphere | $SiO_2/SiC/C$ |
| | | 2. Under reactive amine atmosphere | $Si_2ON_2/SiO_2$ |
| | | 3. Under $O_2$ | $SiO_2$ |
| | C. | React product of III.A. with an organometallic complex $ML_a$, in the presence of a catalyst | $[RSiHO]_l[RSiO]_m$<br>       |<br>    $L_bM$—O |
| | D. | Pyrolyze product of III.C. | |
| | | 1. Under $O_2$ | $M_xSi_yO_z$ |
| | | 2. Under reactive amine atmosphere | $M_xSi_yO_zN_w$ (e.g., "Sialon") |
| IV. | A. | Substitute with hydrocarbon: catalytically react with a compound containing an unsaturated carbon=carbon bond | $[RSiHO]_l[RSiO]_m$<br>       |<br>      R |
| | B. | Pyrolyze | |
| | | 1. Under inert atmosphere | $SiO_2/SiC/C$ |
| | | 2. Under reactive amine atmosphere | $Si_2ON_2/SiO_2$ |
| | | 3. Under $O_2$ | $SiO_2$ |
| V. | A. | Substitute with amine: catalytically react with a secondary amine $NR''_2H$ | $[RSiOH]_l[RSiO]_m$<br>       |<br>      $NR''_2$ |
| | B. | Crosslink with amine: catalytically react with primary amine $NR''H_2$ or ammonia | $[RSiHO]_l[RSiO]_m$<br>       |<br>      N—<br>      |<br>$[RSiHO]_l[RSiO]_m$ |
| | C. | Pyrolyze | |
| | | 1. Under inert atmosphere, or | $Si_2ON_2/SiO_2/SiC/C$ |
| | | 2. Under reactive amine atmosphere | $SiON_2/SiO_2$ |
| | | 3. Under $O_2$ | $SiO_2$ |

TABLE 1-continued

Starting material: Polymer containing the structure [RSiHO]$_n$

| Pathway | Primary Product |
|---|---|
| VI. A. Substitute with organometallic group: | |
|   1. Catalytically react with ML$_a$ | [RSiHO]$_l$[RSiO]$_m$<br>        |<br>       LML$_{a-1}$<br>or<br>[RSiHO]$_l$[RSiO]$_m$<br>        |<br>       ML$_b$ |
|   2. Catalytically react with L$_a$M—OH | [RSiHO]$_l$[RSiO]$_m$<br>        |<br>      OML$_b$ |
| B. Pyrolyze products of either VI.A.1. or VI.A.2. | |
|   1. Under O$_2$ | M$_x$Si$_y$O$_z$ |
|   2. Under reactive amine atmosphere | M$_x$Si$_y$O$_z$N$_w$ |
| VII. React with coupling agent H—Z—H | |
|   1. ─(RSiHO)$_n$─ | [RSiO]<br>  |<br>  Z |
|   2. Cyclomeric starting material<br>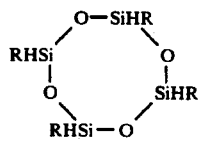 | [RSiO]<br>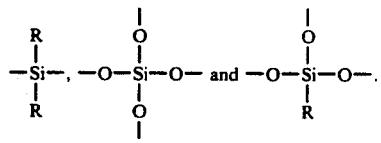 |

The hydridosiloxane starting material is a polymer which contains recurring mer units having the structure —[RSiHO]—, i.e., —[RSiHO]$_n$— wherein n indicates the number of recurring mer units in the polymer, and wherein R is selected from the group consisting of: hydrogen; hydroxyl; C$_1$-C$_{10}$ alkyl or alkoxy, which may be either unsubstituted or substituted with hydroxyl, lower alkyl, lower alkoxy, halogeno, silyl, or NR''$_2$ groups, wherein R'' is hydrogen or lower alkyl; aryl of 1-2 rings, which may be similarly substituted; NR$_2$''; silyl; and ML$_a$, OML$_a$, or NR''ML$_a$, wherein ML$_a$ is an organometallic compound, and may be an oligomer or cluster. This hydridosiloxane starting material will frequently be commercially available, or it may be synthesized from an unsubstituted monomeric or polymeric hydridosiloxane using the catalytic Si—H bond activation/substitution reaction described herein. Cyclomers such as $$\begin{array}{c} O-SiHR \\ RHSi \quad\quad O \\ | \quad\quad\quad | \\ O \quad\quad SiHR \\ RHSi-O \end{array}$$

may be used as well, as may hydridosiloxane copolymers. Suitable hydridosiloxane copolymers include the mer unit —[RSiHO]—, as above, combined with other types of monomers to improve polymeric and pyrolytic properties. Any such copolymers are considered to be equivalent, for purposes of the invention, to the homopolymer —[RSiHO]$_n$—. Preferred monomer units for incorporation into a hydridosiloxane copolymer include but are not limited to, the following structures (wherein R is as defined above):

$$-\underset{\underset{R}{|}}{\overset{\overset{R}{|}}{Si}}-, \quad -O-\underset{\underset{O}{|}}{\overset{\overset{O}{|}}{Si}}-O- \quad\text{and}\quad -O-\underset{\underset{R}{|}}{\overset{\overset{O}{|}}{Si}}-O-.$$

It is required that the aforementioned reactions for preparing ceramic precursors be carried out in the presence of a catalyst. Virtually any catalyst may be used, so long as it does not actively interfere in the reaction and is effective to the activate Si—H bonds of the precursor. Suitable catalysts include acid catalysts such as HCl, H$_2$SO$_4$, HBr, NH$_4$Cl, NH$_4$Br, AlCl$_3$, BCl$_3$ and H$_3$PO$_4$, basic catalysts such as NaOH, KOH, Ca(OH)$_2$, NH$_3$ and pyridine, and metal catalysts, particularly transition metal catalysts such as those indicated in Tables 2 and 3 below. Table 2 sets forth homogeneous catalysts which dissolve in the reactants. Heterogeneous catalysts such as those of Table 3 may also be used, as can mixtures of homogeneous catalysts and/or heterogeneous catalysts. (It should be pointed out here that the "homogeneous" and "heterogeneous" classifications are made on the basis of solubility in common organic solvents such as alcohols. However, it is not uncommon that during the reactions, homogeneous catalysts may be converted to a heterogeneous form and vice versa.) These catalysts may include any number of ligands, usually 1-6, including carbonyl, amino, halo, silyl, hydrido, phosphine, arsine and organic ligands.

The reaction involving catalytic activation of Si—H bonds in the hydridosiloxane starting material —[RSiHO]$_n$— is preferably carried out under an inert atmosphere, e.g., under argon, nitrogen, or the like. Also, since the reaction can be an aggressive, it is preferred that it be carried out at temperatures of 0° C. to 100° C., more preferably 0° C. to 40° C. The use of an inert organic solvent, is optional.

The catalyst(s) may be supported on a polymer, inorganic salt, carbon or ceramic material or the like. The heterogeneous catalyst may be provided in a designated shape, such as in particles, as porous plates, etc.

The concentration of catalyst will usually be less than or equal to about 5 mole percent based on the total number of moles of reactants, usually between about 0.1 and 5 mole percent. In some instances, however, catalyst concentration will be much lower, on the order of 20 to 200 ppm.

TABLE 2

Homogeneous Catalysts

H$_4$Ru$_4$(CO)$_{12}$, Fe(CO)$_5$, Rh$_6$(CO)$_{16}$, Co$_2$(CO)$_8$, (Ph$_3$P)$_2$Rh(CO)H, H$_2$PtCl$_6$, nickel cyclooctadiene, Os$_3$(CO)$_{12}$, Ir$_4$(CO)$_{12}$, (Ph$_3$P)$_2$Ir(CO)H, NiCl$_2$, Ni(OAc)$_2$, Cp$_2$TiCl$_2$, (Ph$_3$P)$_3$RhCl, H$_2$Os$_3$(CO)$_{10}$, Pd(Ph$_3$P)$_4$, Fe$_3$(CO)$_{12}$, Ru$_3$(CO)$_{12}$, transition metal hydrides, transition metal salts (e.g., ZnCl$_2$, RuCl$_3$, NaHRu$_3$(CO)$_{11}$) and derivatives, PdCl$_2$, Pd(OAc)$_2$, ($\phi$CN)$_2$PdCl$_2$, [Et$_3$SiRu(CO)$_4$]$_2$, (Me$_3$Si)$_2$Ru(CO)$_4$, [Me$_2$SiXSiMe$_2$]Ru(CO)$_4$, and mixtures thereof.

TABLE 3

Heterogeneous Catalysts

Pt/C, Pt/BaSO$_4$, Cr, Pd/C, Co/C, Pt black, Co black, Ru black, Ra—Ni, Pd black, Ir/Al$_2$O$_3$, Pt/SiO$_2$, Rh/TiO$_2$, Rh/La$_2$O$_3$, Pd/Ag alloy, LaNi$_5$, PtO$_2$, and mixtures thereof.

B.2. Substitution of —[RSiHO]$_n$— With Alkoxy Moieties

The preferred method of the present invention involves preparation of a polysiloxane preceramic by reaction of a hydridosiloxane polymer with an alcohol. The reaction involves catalytic activation of Si—H bonds in the hydridosiloxane starting material, and replacement of the "activated" hydrogen atoms therein with alkoxy groups, as indicated in Section II of Table 1.

The hydridosiloxane may be represented as containing one or more mer units having the structure

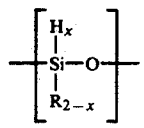

wherein x is 1 or 2. Reaction of this starting material with a hydroxyl-containing reactant R'OH, wherein R' is hydrogen or a lower alkyl moiety and is different than R, yields the polysiloxane preceramic

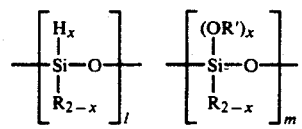

in which, as may be deduced from the structure, hydrogen atoms of the hydridosiloxane starting material have been replaced by new, OR', alkoxy moieties. The relative amounts of unsubstituted and alkoxy-substituted mer units are indicated by the subscripts l and m, respectively. (Reaction with water, i.e., wherein R' is hydrogen, is described in Section B.6. below.)

This preceramic may be pyrolyzed directly to give the products enumerated in Table 1. Alternatively, it may be processed prior to pyrolysis according to the sol-gel method described in Section B.5., below, to give a preceramic gel (see Section II of Table 1). The gel, while yielding the same ceramic product as its linear precursor, provides higher ceramic yields and does not melt upon pyrolysis.

In a related reaction, the hydridosiloxane starting material is monomeric rather than polymeric, and initially substituted with alkoxy groups, i.e., it is a monomeric silane substituted with one, two or three alkoxy groups "OR$^1$". The monomeric silane may thus be represented by the formula H$_m$Si(OR$^1$)$_{4-m}$ wherein m is 1, 2 or 3. In a first type of reaction involving this monomeric starting material, the compound is reacted with an alcohol R$^2$OH in the presence of a catalyst effective to activate Si—H bonds so that activated hydrogen atoms are replaced by new alkoxy moieties "OR$^2$". R$_1$ and R$_2$ are typically C$_1$-C$_{10}$ alkyl or alkoxy moieties, or aryl of 1-4, preferably 2-3 rings, more typically lower alkyl groups, and may be either unsubstituted or substituted as for the substituent "R", discussed above. The resulting structure may be represented as Si(OR$^1$)$_{4-m}$(OR$^2$)$_m$.

This latter compound may be hydrolyzed to give a polysiloxane ceramic precursor; hydrolysis will again be carried out in the presence of a catalyst effective to activate Si—H bonds. The differential in hydrolysis rates of the two different types of alkoxy moieties —OR$^1$ and —OR$^2$ is useful in dictating the type of polymer which result upon gelation (i.e., upon hydrolysis). Where there is a substantial difference in hydrolysis rates, a more linear polymer will be produced, while if hydrolysis rates are approximately the same (for example, when R$_1$ and R$_2$ represent the same substituents), a crosslinked structure will result.

(A second type of reaction involving the aforementioned monomeric silane is simple hydrolysis to give a polymeric alkoxy-substituted siloxane, containing pendant —OR$^1$ moieties.)

B.3. Introduction of additional carbon: When the ceramic product ultimately desired is to include carbon, e.g., as silicon carbide, it is preferred that the polysiloxane ceramic precursor be modified to increase the mole fraction of carbon therein. In such a case, as illustrated in Section IV of Table 1, the hydridosiloxane starting material —[RSiHO]$_n$— is reacted, in the presence of a catalyst effective to activate Si—H bonds, with a compound containing an unsaturated carbon-carbon bond. The compound may be alkenyl or alkynyl, and of any size and containing any number and kind of substituents, so long as potential steric interference is minimized and the substituents do not hinder the reaction. In general, the reaction may be represented as introducing pendant —(CH$_2$)$_2$—R species in place of the activated hydrogen atoms, by reaction with —CH=CH—R (or —C≡C—R) with R as defined hereinabove.

Pyrolysis of the carbon-rich polysiloxane precursor will give ceramic products as indicated in Table 1, Section IV.

B.4. Amine substitution: When it is desired that the ceramic material include nitrogen, e.g., as silicon nitride or silicon oxynitride, the hydridosiloxazane starting material —[RSiHO]— is reacted with ammonia or a primary or secondary amine in which the substitutents, if any, are lower alkyl, in the presence of a catalyst effective to activate Si—H bonds. When the amine reactant is a secondary amine, the reaction will result in a structure in which the linearity of the siloxane polymer is substantially maintained, but in which the activated hydrogen atoms in the starting material have been replaced by pendant amine groups. When the amine reactant is ammonia or a primary amine, a crosslinked siloxazane structure in which polysiloxane chains are joined through —NH— or —NR"— linkages results (Section V of Table 1). Additional information concerning this latter reaction may be found in parent application Ser. No. 012,874, incorporated by reference hereinabove.

Pyrolysis of either the linear or crosslinked ceramic precursor in which nitrogen-containing moieties have been incorporated as above will result in: (1) a mixture of silicon oxynitride, silica, silicon carbide and carbon, when pyrolysis is conducted in an inert atmosphere; (2) a mixture of silicon oxynitride and silica, when pyrolysis is conducted in a reactive amine atmosphere, e.g., in ammonia or methylamine; (3) silica, when pyrolysis is conducted in oxygen.

B.5. Substitution with organometallic species: In an equally important embodiment of the present invention, organometallic species are introduced into the polysiloxane precursor prior to pyrolysis. Pyrolysis will then give metal silicates, which (depending on the pyrolysis atmosphere) may or may not contain nitrogen.

Several routes may be taken to introduce organometallic species into the polysiloxane precursor. First, the hydridosiloxane starting material —[RSiHO]$_n$— may be directly reacted with an organometallic compound ML$_a$, wherein M is a metal atom, L represents one or more ligands associated therewith, and "a" represents the mole ratio of L to M in the compound. "ML$_a$" may be monomeric or oligomeric; it may also represent a cluster. As above, the reaction is carried out in the presence of a catalyst effective to activate Si—H bonds, so that the activated hydrogen atoms are replaced with the organometallic species. Depending on the particular metal and ligand, the activated silicon atoms may bind either to the metal or to the ligand, to give either Si—M or Si—L bonds in the resultant ceramic precursor.

Examples of representative "M" elements include lithium, sodium, potassium, magnesium, calcium, boron, aluminum and phosphorus, as well as the transition metals, lanthanides and actinides. Examples of suitable ligands include carbonyl, cyanocyclopentadienyl ("Cp"), phenyl ("Ph"), halide, metal clusters, alkoxy, and $\alpha$C=C$\alpha$, where $\alpha$ is alkyl, particularly lower alkyl, or aryl, such as phenyl.

Second, the hydridosiloxane starting material —[RSiHO]$_n$— may be reacted: (1) with water, as described above, to give pendant hydroxyl groups in the ceramic precursor; and subsequently (2) with the organometallic compound ML$_a$. In this case, in contrast to the reaction just described, the organometallic species bind to the silicon atoms of the polysiloxane chain via oxygen bridges, i.e., Si—H bonds are replaced by Si—OML$_b$ linkages, wherein b represents the mole ratio of L to M in these pendant groups.

Third, the hydridosiloxane starting material —[RSiHO]$_n$— may be directly reacted with a compound ML$_a$—OH or M—OH, i.e., a metal-containing compound which includes one or more hydroxyl groups. As before, the reaction is carried out in the presence of a catalyst effective to activate Si—H bonds. The ceramic precursor which results here is similar to that obtained in the reaction just described, in which Si—H bonds are replaced by Si—OML$_b$ linkages. Examples of metal-containing compounds suitable for this reaction include CpFeCp—OH, Cp$_2$Ti(OH)$_2$, NaOH, KOH, R$_3$Si—OH, R$_2$B—OH, and the like, wherein R is as defined earlier herein.

Pyrolysis of ceramic precursors which have been modified to include organometallic groups yields metal silicates that may be represented by the formula M$_x$Si$_y$O$_z$. Pyrolysis under an amine atmosphere, or of a precursor that has been additionally modified to include nitrogen (as described above), will yield a metal-containing silicious ceramic material that additionally contains nitrogen, M$_x$Si$_y$O$_z$N$_w$, wherein x, y, z and w represent the combining proportion of M, Si, O and N in the ceramic product.

B.6. Sol-gel processing: The alkoxy-substituted hydridosiloxane prepared in Section B.2. may, if desired, be processed using sol-gel techniques. The reaction is a hydrolysis step carried out using conventional sol-gel processing methodology as described, for example, by C.J. Brinker et al., in "Better Ceramics Through Chemistry", eds. C. J. Brinker et al., Mat. Res. Soc. Symposium Proceedings 32 (1984), at page 25, cited above. Hydrolysis introduces pendant hydroxyl groups into the polysiloxane structure as well as some degree of coupling or cross-linking. The product obtained may be either pyrolyzed directly (see Section C) or substituted as described in the preceding sections.

As with the reactions described in Sections B.2. through B.5., hydrolysis is typically carried out at a temperature in the range of about 0° C. to 40° C., preferably at room temperature or lower. The reaction medium is typically aqueous alcohol, and the preferred mole ratio of water to hydridosiloxane starting material is on the order of 0.1 to 8, more preferably 0.1 to 4, most preferably 0.1 to 2. Increasing the amount of water present will typically give a more crosslinked product, while reducing the amount of water will correspondingly give a more linear product. The reaction is carried out catalytically, with Lewis acid or base catalysts preferred. Examples of suitable catalysts for this reaction are as set forth above.

B.7. Reaction with a coupling agent: If desired, the polymer obtained upon catalytic Si—H bond activation and substitution may be further reacted with a coupling agent H—Z—H as defined above. Such a reaction provides —Z— bridges between hydridosiloxane units (which may be either oligomeric, polymeric or cyclomeric), either extending the degree of polymerization of or crosslinking the product.

Alternatively, a monomeric, oligomeric or cyclomeric hydridosiloxane starting material, (e.g., a cyclomeric material as described in Section B.1.), may be directly treated with a coupling agent H—Z—H in a dehydrocoupling reaction to give a coupled hydridosiloxane product. The coupled product may be pyrolyzed as is, substituted first using the reactions of B.2. through B.5., or processed via a sol-gel method as described in Section B.6.

These latter two reactions are illustrated schematically in Section VII of Table 1.

C. Pyrolysis.

Another important advantage of the compositions and methods of the present invention is the specificity and degree of ceramic yield upon pyrolysis. Generally, an increase in the oxygen content of the ceramic precursor will result in a higher oxygen content in the ceramic product, while an increase in the carbon content of the precursor will result in a higher carbon content in the ceramic product. In addition to the chemical composition of the ceramic precursor, the atmosphere in which pyrolysis is conducted (as well as the pyrolysis temperature) also dictates the composition of the ceramic product. Ceramic materials which may be obtained by the present method include, inter alia, silica, silicon carbide, silicon nitride, silicon oxynitride, and metal silicates. In a particularly preferred embodiment, silica is prepared in substantially pure form.

Silica will be provided by pyrolysis of a ceramic precursor containing Si and O in oxygen or in an oxygen-containing atmosphere. Carbon-free polysiloxanes which may be prepared according to the method disclosed herein will provide silica of very high purity, i.e., 98–99% or higher.

The ceramic precursors prepared according to the methods described in Section B may also be pyrolyzed to give silicon nitride, silicon oxynitride, silicon carbide, and metal silicates, as described above and as outlined in Table 1.

Procedurally, pyrolysis is preferably carried out as follows. A ceramic precursor prepared as described in Section B is heated in the selected atmosphere at a predetermined heating rate. If it is desired that the composition of the pyrolysis product correspond substantially to the composition of the precursor, pyrolysis should be carried out in an inert atmosphere. If desired, pyrolysis may be carried out in a reactive atmosphere, e.g., under $O_2$, $NH_3$, $H_2O_2$, $H_2O$, $N_2O$, $H_2$, an alkylamine or the like. Pyrolysis in a reactive amine atmosphere (i.e., under ammonia or an alkylamine gas) will typically give more nitrogen in the ceramic product, e.g., in the form of silicon nitride or silicon oxynitride. Preferred heating rates for bulk pyrolysis are in the range of about 0.1° C. to 10° C. per minute, preferably about 0.5° C. to 2° C. per minute, with a particularly effective heating rate, optimizing ceramic yield, of about 0.5° C. per minute. In some applications, flash pyrolysis may be preferred (e.g., in coating applications).

Pyrolysis is carried out at temperatures of at least about 500° C, preferably at temperatures in the range of about 500° C. to about 900° C. The pyrolysis products set forth in Table 1 represent the ceramic materials obtained by pyrolyzing in this temperature range. In some cases, it may be desirable either to initially pyrolyze at a higher temperature, e.g., 1200° C or higher, or to carry out an additional high temperature pyrolysis step (again, at greater than about 1200° C.) after the initial, 500° C. –900° C., pyrolysis. Such a procedure is useful to remove residual carbon, and in carborizing or recrystallizing the product. Where mixtures of silicious ceramic products (e.g., silica, silicon oxynitride) and carbon are obtained upon pyrolysis in the 500° C. to 900° C. range, a subsequent high temperature pyrolysis step will give silicon carbide in high yield. Silicon carbide will also be obtained in fairly high yield upon initial high temperature pyrolysis of the carbon-containing ceramic precursors disclosed hereinabove.

The heating process may include one or more isothermal holding steps, in order to control the pyrolysis, to provide more crosslinking at moderate temperatures (less than about 400° C.) and to further increase the yield of the final product.

After pyrolysis at a relatively low temperature, i.e., in the range of 500° C. to 900° C., a high temperature pyrolysis step may be carried out to convert mixtures of silica and carbon to silicon carbide or to crystallize an amorphous ceramic product. Mixtures of silica and carbon are obtained, for example, by low temperature pyrolysis of the precursors of Section B 1. and B.2. If desired, pyrolysis may be carried out in the presence of a catalyst; examples of suitable catalysts are set forth in Tables 2 and 3.

Optionally, pyrolysis may be carried out only partially, i.e., in applications where it is not necessary to obtain a fully pyrolyzed material. Such "partial pyrolysis" or partial curing may be carried out at temperatures lower than 500° C.

D. Ceramic Coatings.

The ceramic materials provided herein are useful in a number of applications, including as coatings for many different kinds of substrates.

Silica, silicon nitride and silicon carbide coatings may be provided on a substrate, for example, by a variation of the pyrolysis method just described. A substrate selected such that it will withstand the high temperatures of pyrolysis (e.g. metal, glass, ceramic, fibers, graphite) is coated with the preceramic gel material. The ceramic precursor is then pyrolyzed on the substrate by heating according to the pyrolysis procedure outlined above. In such a method, pyrolysis can be conducted relatively slowly, i.e., at a heating rate between about 0.1° C. and 10.0° C. per minute, in order to allow evolved gas to escape gradually, and can include one or more isothermal holding steps. In some instances, for example, with relatively temperature-sensitive materials, or where a rapid-coating process is desired, a flash pyrolysis step may be preferred. Flash pyrolysis involves either direct exposure of a coated substrate to a high temperature, or application of the coating material to the surface of a heated substrate. Repeated, multiple coatings may be applied where a thicker layer of material is desired, with partial curing or gradual or flash pyrolysis following each individual coating step.

The pyrolysis temperature will vary with the type of coating desired. Typically, temperatures will range from about 350° C. to about 1100° C. Lower temperatures, below about 500° C., can result in only partially pyrolyzed polymer.

The above coating procedure is a substantial improvement over the conventional, chemical vapor deposition (CVD) method of producing silicious coatings in which the appropriate compounds (e.g., $SiH_4$ and $NH_3$ or volatile silazane) react in the vapor phase to form the ceramic which deposits on the target substrate. CVD is typically a time-consuming process which requires costly and specialized equipment that is limited in size. The procedure described above for producing coatings containing silica, silicon nitride, silicon oxynitride, and/or silicon carbide can be done with a conventional furnace. Further, the method leads to heat-stable, wear—, erosion—, abrasion, and corrosion-resistant silicious ceramic coatings. Because these silicon-containing coatings have desirable electronic and optical properties, and are resistant to most chemicals as well as to extremes of temperature, many applications of the coating process are possible. One specific application is in gas turbine engines, on parts which are particularly susceptible to wear, corrosion, or heat. Also, the coating process could be used to make the dielectric material of capacitors, or for providing insulating coatings in the electronics industry. Other applications are clearly possible.

E. Fabrication of Molded Ceramic Bodies

The ceramic precursors prepared as described hereinabove may also be used to form three-dimensional articles by injection- or compression-molding using procedures substantially as described in co-pending application Ser. No. 012,874, previously incorporated reference. The results as demonstrated in the examples of those applications indicate that the procedure may also be successful in the absence of sintering agents.

F. Preparation of Fibers

The ceramic precursors can also be used for preceramic fiber spinning.

Three general spinning techniques are commonly used: (a) melt spinning, in which the polymer is spun from its melt and solidified by cooling; (b) dry spinning, in which the polymer is at least partially dissolved in solution and pulled out through the spinneret into a heat chamber, then solidified by solvent evaporation; and (c) wet spinning, in which a concentrated polymer solution is spun into a coagulation or regeneration bath containing another solvent in which the polymer is not soluble. In addition, gel-type polymers can be spun from very viscous solutions. These tractable polymers rapidly gel and crosslink upon removal of solvent after spinning due to high latent reactivity. Polymeric fibers so formed are intractable.

Additional, relatively small quantities (0.1–5.0 wt. %) of a very high molecular weight substantially linear organic polymer (100,000–5,000,000D) may be mixed with the inorganic polymer to support improve the fiber strength after spinning, as taught in, e.g., U.S. Pat. Nos. 3,853,567 to Verbeek and 3,892,583 to Winter et al.

The supporting technique is especially useful when low molecular weight and/or nonlinear polymers having a very low degree of chain entanglement are used.

One problem encountered in ceramic fiber fabrication derives from the fusability of inorganic polymers during pyrolysis. This fusability results in structural problems in the spun fiber. Polymers produced by the present invention, however, may overcome the fusability problem, providing that the catalytic process as described herein is actually incorporated into the fiber-spinning process. For example, a high molecular weight polysiloxane may be mixed with a homogeneous catalyst and heated in a spinneret or in a curing chamber to cause Si—H bond activation to occur and increase the degree of crosslinking in the fiber. Alternatively, the spinneret can itself be a catalytic bed. Coupling or crosslinking agents may also be included in the fiber-spinning process. Latent reactive groups (e.g., free amino moieties) may be present as well.

G. Other Applications

Many other applications of the novel polymers of the invention are clearly possible.

Combining the polysiloxane gels prepared in Section C with other ceramic powders (e.g., SiC, BN, $B_4C$) may be carried out in order to produce composite articles. Such a composite of, e.g., a siloxane polymer/SiC powder mixture may give an article having improved oxidation resistance. Another application would be to use the polymer gels as binders combined with ceramic powders so as to provide a fluid polymer/powder solution.

It is to be understood that while the invention has been described in conjunction with the preferred specific embodiments thereof, that the foregoing description as well as the examples which follow are intended to illustrate and not limit the scope of the invention, which is defined by the scope of the appended claims. Other aspects, advantages and modifications within the scope of the invention will be apparent to those skilled in the art to which the invention pertains.

EXAMPLES

Experimental: Unless otherwise indicated, the reagents used were obtained from the following sources: silanes, from Petrarch Systems, Inc., Bristol, Pa.; organic reagents including amines, from Aldrich Chemical Co., Milwaukee, Wis.; gases, from Matheson, Seacaucus, N.J.; and catalysts, from Strem, Newburyport, Mass.

EXAMPLE 1

Reactions of Oligo and Polymethylsiloxane with Ammonia a. 0.05 mmol (32 mg) $Ru_3(CO)_{12}$ was added to 100 mmol (6.0 g) $[CH_3SiHO]_4$ and the solution was heated at 60° C. under 200- psi of ammonia. Gas evolution gave a pressure of 400 psi in 19 hours and hard rubber was formed. The product's elemental analysis showed the presence of 5.55% N which indicated a nitrogen-silicon ratio of 0.28 (Table 3). The ratio of oxygen to silicon was found to be about 1.29. Some of the oxygen excess was believed to be a result of oxygen contamination found in the commercial starting material and detected by an NMR intensity ratio of Si—H/Si—$CH_3$ absorbance (0.8:1.0).

The product was pyrolyzed at 850° C. under and atmosphere first, of nitrogen and then, of ammonia. Elemental analysis of the pyrolyzed material suggested a mixture of the following ceramic components (mol ratio): $SiO_2(0.63)$; $Si_3N_4(0.23)$; SiC(0.14); C(0.58). It is not clear whether the N content derived from silicon nitride or from silicon oxynitride. The mol ratios of O, N and Si in the ceramic material were similar to those of the preceramic polymer, i.e., prior to pyrolysis. Pyrolysis under a slow stream of ammonia reduced, almost totally, the carbon content, as well as reducing some of the oxygen excess. Correlatively, pyrolysis under ammonia increased significantly the nitrogen content.

Very similar results were observed when the cyclotetramer was replaced by polymethylsiloxane having a number average molecular weight (Mn) of 1880D (degree of polymerization is 29) as shown in Tables 4 and 5. A comparison of the cyclo- and polysiloxane reactions reveals that less nitrogen interacts with the polymer than with the cyclomer, and that the SiC fraction in the product obtained by pyrolysis under nitrogen is higher for the polymer reaction. However, no real difference was seen when both were pyrolyzed under ammonia. The ceramic yields were found to be very high for all types of reactions and pyrolysis procedures. (see Table 4).

b A solution of 100 mmol 6.0 g) [CH₃SiHO]₄ and 25.0 μmol (8 mg) Ru₃(CO)₁₂ was heated at 60° C. under 100 psi of ammonia. After 2 hours 220 psi of pressure were formed, and the product was a viscous liquid having M$_n$=1230 D. The pressure was released and the reaction mixture was recharged with additional 100 psi of ammonia. 200 psi of gas were evolved in a 2-hour period, and the viscous liquid converted to a soft rubber.

¹H-NMR integration revealed that 41% of the Si—H bonds were replaced by ammonia to form Si—NH₂ and Si—NH groups.

Elemental analysis showed the incorporation ratio of 0.24 nitrogen per carbon atom, which indicated the formation of cyclosiloxane chain polymer bridged by ammonia.

Indeed, a dimer of two cyclotetramers bridged by a single —NH was the major product found by GC—MS analysis.

IR of CCl₄ solutions showed new sharp stretch peaks at 3421 (w), 3380 (m), cm⁻¹ together with new shoulders at 1240 and 1160 cm⁻¹.

¹H NMR (CDCl₃, δ, Ref CHCl₃: Si—H (4.69, 0.59H), NH (1.10, 0.16H) CH₃ (0.22, 3H).

The elemental analysis of the product was as follows: C, 19.91 (mol ratio 1.00); H, 6.14 (mol ratio 3.70); N, 5.39 (mol ratio 0.24); S, 42.23 (mol ratio 0.91).

TABLE 4

The Elemental Analysis of Polymers and Ceramics Obtained in a Catalyzed Reaction Between Methylsiloxanes and Ammonia

| Product | Analysis % (mol ratio) | | | | |
|---|---|---|---|---|---|
| | Si | O | N | C | H |
| Cyclotetramer reaction | | | | | |
| Polymer | 40.70 | 29.85 | 5.55 | 18.02 | 5.88 |
| | (1.00) | (1.29) | (0.28) | (1.03) | (4.06) |
| Ceramic material under N₂ | 45.73 | 32.53 | 6.94 | 14.10 | 0.79 |
| | (1.00) | (1.25) | (0.31) | (0.72) | (0.48) |
| Ceramic material under NH₃ | 47.76 | 28.26 | 21.81 | 1.35 | 0.57 |
| | (1.00) | (1.04) | (0.91) | (0.06) | (0.33) |
| Polymer Reaction | | | | | |
| Polymer | 42.47 | 27.80 | 4.06 | 19.67 | 6.00 |
| | (1.00) | (1.14) | (0.19) | (1.07) | (3.95) |
| Ceramic material under N₂ | 48.12 | 32.81 | 5.02 | 13.65 | 0.76 |
| | (1.00) | (1.19) | (0.21) | (0.66) | (0.44) |
| Ceramic material under NH₃ | 49.29 | 28.35 | 21.01 | 1.75 | 0.54 |
| | (1.00) | (1.03) | (0.87) | (0.09) | (0.31) |

TABLE 5

Ceramic Yield of the Pyrolyzed Polymers Obtained in a Catalytic Reaction Between Methylsiloxanes and Ammonia

| Reactant | Pyrolysis Conditions | Ceramic Yield (%) |
|---|---|---|
| Cyclotetramer | N₂ | 77 |
| Cyclotetramer | NH₃ | 84 |
| Polymer | N₂ | 75 |
| Polymer | NH₃ | 88 |

Evidence for Si₂ON₂: X-ray powder diffraction analyses of the ceramic products obtained by the above procedure showed clear spectra pattern of orthorhombic Si₂ON₂, when the polymeric products were pyrolyzed under NH₃. Pyrolysis under N₂ gave poor crystallization under the same conditions. When the amorphous ceramic product produced by pyrolysis under N₂ at 900° C. was reheated to 1600° C. (also under N₂), however, X-ray powder diffraction analysis of the product again indicated orthorhombic Si₂ON₂. No other types of ceramic crystallites were observed in the X-ray powder diffraction spectra.

EXAMPLE 2

Reactions of Methylsiloxanes [CH₃SiHO]$_x$ With Dimethylamine a. [CH₃SiHO]₄: To 6.0 g (100 mmol) [CH₃SiHO]₄ were added 32 mg (0.05 mmol) of Ru₃(CO)₁₂ and the solution was charged with approximately 100 psi of dimethylamine. The reaction was carried out at 60° C. and detected by the observed pressure formed in the reactor. The pressure was released every 0.5–1 hour and the reactor recharged with fresh dimethylamine. After 6 hours, a total pressure of 1100 psi was charged into the reactor and a total pressure of 770 psi was formed. No more gas evolution was observed. 8.1 g of viscous oily products were obtained, indicating a 49% yield of amine substitution. This yield correlated with the ¹H—NMR analysis of the solution, which showed 53% amine substitution and 29% Si—H groups. GC—MS analysis showed that bis- and tris-substituted cyclotetramers were the major products when mono and tetrakis appear only in small quantities.

b. [CH₃SiHO]₃₁: The reaction was run with the same amounts and under the same conditions as the reaction with the tetramer. Only 50 psi of dimethylamine could be charged into the reactor each time. A total pressure of 500 psi was charged and 375 psi of gas evolved after 6 hours. 7.4 g of a very viscous polymer was obtained (33% yield of amine substitution) which is correlated to the ¹H—NMR analysis showing similar results (36% amine substitution and 45% Si—CH₃ groups).

EXAMPLE 3

Reactions of Methylsiloxanes [CH₃SiHO]$_x$ a. [CH₃SiHO]₄: To 6.0 g (100 mmol) [CH₃SiHO]₄ were added 0.40 g water and Ru₃(CO)₁₂ as above. The reaction was carried out at 60° C. under nitrogen and detected by the observed hydrogen pressure formed in the reactor. After ½ hour, a total pressure of 440 psi was formed. After 2 hour, a total pressure of 520 psi was observed. No more gas evolution was observed. Pyrolysis was carried out at a rate of 5° C./min up to 900° C. Pyrolysis under nitrogen gave a 70% yield, while pyrolysis under ammonia gave a 77.3% yield. Elemental analysis of the product before pyrolysis gave the following: C, 19.91 (mol ratio 1.03); H, 5.67 (mol ratio 3.81); N, 0.10; Si, 41.63 (mol ratio 1.00); O, 22.16 (mol ratio 0.93). Elemental analysis of the product after pyrolysis under nitrogen gave: C, 12.66 (mol ratio 0.65); H, 0.98 (mol ratio 0.60); N, 0.74 (mol ratio 0.03); Si, 45.74 (mol ratio 1.00); O, 40.27 (mol ratio 1.54). The mole ratio of SiO₂: SiC:C was derived to be approximately 0.77:0.23:0.42.

b. [CH₃SiHO]₂₉: To 6.0 g (100 mmol) [CH₃SiHO]₄ were added 0.18 q water and Ru₃(CO)₁₂ as above. The reaction was carried out at 60° C. under nitrogen and, as in Section (a), detected by the observed pressure formed in the reactor. After ½ hour, a total pressure of 150 psi was formed. After 2 hour, a total pressure of 180 psi was observed. No more gas evolution was observed. Pyrolysis was carried out at 900° C. Pyrolysis under nitrogen gave a 44% yield, while pyrolysis under ammonia gave a 86.7% yield. Elemental analysis of the product before pyrolysis gave the following: C, 20.69 (mol ratio 1.13); H, 6.70 (mol ratio 4.41); N, 0.24; Si, 42.78 (mol ratio 1.00); O, 26.81 (mol ratio 1.07). Elemental analysis of the product after pyrolysis under nitrogen gave: C, 12.73 (mol ratio 1.06); H, 0.82 (mol ratio 0.82); N, 0.80 (mol ratio 0.06); Si, 45.53 (mol ratio 1.63); O, 40.41 (mol ratio 2.52).

c. To 10 grams of cyclotetrahydridomethylsiloxane $(CH_3SiHO)_4$, in 20 g tetrahydrofuran (THF) were added 0.67 g $H_2O$ and 20 mg $Ru_3(CO)_{12}$, and the solution was heated to 60° C. under nitrogen. The reaction was followed by observing the total pressure in the reactor. After 15 minutes, the total pressure observed was 280 psi; after 3 hours, the increase in pressure stopped and the evolution of gas ($H_2$, as above) was thus completed. After removal of solvent, a viscous, waxy polymer, polycyclohydridomethylsiloxane (PHMSO) was obtained, removed from the reactor, and diluted to give a 5 wt. % solution. The polymer slowly continued to crosslink and converted to a solid product which was still soluble in THF. The resulting polymer can be pyrolyzed under nitrogen or oxygen to give a high yield of an amorphous ceramic composition comprising silica and potentially carbon, and is useful in the fabrication of ceramic coatings, shaped products, fibers, films, and the like.

EXAMPLE 4

Reactions of Diethylsilane with Water a. To 0.88 g diethylsilane were added 0.18 g $H_2O$ and 50 mg triethylamine as catalyst. The reaction was carried out under nitrogen at 60° C. and detected by the observed pressure formed in the reactor. After 1 hour, a total pressure of 5 psi was observed. After 22 hours, 78% of the diethylsilane was converted to linear and cyclic oligomers of $Et_2SiO_n$ (Et=ethyl, wherein n is 2-9.

b. To 1.76 g diethylsilane were added 0.36 g water and 16 mg $Ru_3(CO)_{12}$ as catalyst. The reaction was carried out under nitrogen at 60° C. and detected by the observed pressure in the reactor. After 1 hour, a total pressure of 150 psi was observed; a pressure of 150 psi remained after 3 hours. 1.75 g product was obtained. After 1 hour, a series of

EXAMPLE 5

As described in Section B.2., it will sometimes be desired to introduce additional carbon into the preceramic polysiloxane so that a higher fraction of carbon will be present in the ceramic product, e.g., as follows.

a. Reaction of $[CH_3SiHO]_4$ with an alkene or alkyne: To $[CH_3SiHO]_4$ in a suitable solvent such as THF is added a predetermined amount of the selected alkene or alkyne. The amount will vary depending on the mole fraction of carbon desired in the ultimate ceramic product. A catalyst such as $H_2PtCl_6$ is added, and the solution is heated to about 60° C. under an inert atmosphere such as nitrogen. The resulting hydrosilylation product, in which hydrogen atoms of activated Si—H bonds have been replaced by carbon-containing groups, may or may not be isolated at this point. Hydrolysis is then carried out to polymerize this product, according to the method of the preceding examples. Water is added, along with a catalyst, and the reaction is carried out at about 60° C. under nitrogen. As in the preceding examples, the reaction is monitored by observing the increase in pressure during the reaction. When the pressure increase stops, the reaction may be presumed to be complete. Pyrolysis of the resulting polymer will give a product which contains a relatively high fraction of carbon, as either silicon carbide or unbound carbon. To increase the fraction of silicon carbide in the ceramic product, an additional 1200° C. pyrolysis step may be carried out. This procedure is useful for making ceramic articles, coatings, and the like, having a high carbon content.

b. In an alternative procedure, $[CH_3SiHO]_4$ may be hydrolyzed to give a polysiloxane as described in Example 3, followed by reaction with an alkene or alkyne to give substantially the same preceramic polymer as obtained in the Section (a). The catalyst may or may not be the same as that used in Section (a).

c. Aryl groups may also be introduced into the polymer using this method. For example, $[CH_3SiHO]_4$ may be reacted with styrene using essentially the same procedure as described in Section (a), to introduce pendant aromatic groups into the polysiloxane precursor. Alternatively, $[CH_3SiHO]_4$ may first be reacted with water, followed by reaction of the resulting polymer with styrene, along the lines of the procedure outlined in Section (b). In either case, the ceramic precursor produced will have a higher carbon content than that of the hydridosiloxane starting material, in turn giving rise to a ceramic product of higher carbon content (aryl groups are readily transformed to give graphite carbon).

EXAMPLE 6

Ceramic products comprised of metal silicates may be prepared by reacting a hydridosiloxane starting material with a metal-containing compound, as follows.

a. Reaction of PHMSO with CpFeCp—OH: To PHMSO in a suitable solvent such as THF is added a predetermined amount of aluminum bis(glycolate). The amount will vary depending on the mole fraction of iron desired in the ultimate ceramic product. A catalyst such as $Ru_3(CO)_{12}$ is added, and the solution is heated to about 60° C. under an inert atmosphere such as nitrogen. The resulting product, in which Si—H groups have been replaced by

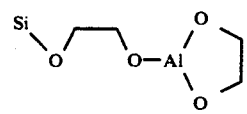

groups, may or may not be isolated at this point. Pyrolysis of the resulting polymer will give an iron silicate ceramic product, i.e., one which contains silicon, iron and oxygen.

b. In an alternative procedure, a linear polyhydridosiloxane starting material is subjected to hydrolysis in dilute solution to form Si—OH species. The product is then reacted with $Ti(OR)_4$ or $(RO)_xTiCl_{4-x}$ to form Si—O—Ti groups.

c. The aforementioned procedures may also be used to prepare "SiAlON", a ceramic product containing aluminum, i.e., in addition to silicon, oxygen and nitrogen. The method of Sections (a) or (b) are followed using an aluminum-containing reactant such as $[RAlNH]_3$, $(RO)_3Al$ or $[RAlO]_3$ instead of aluminum bis(glycolate), with pyrolysis carried out under ammonia.

I claim:

1. A method of preparing a coating of a silicious ceramic material on a substrate, which comprises:
   (a) providing a hydridosiloxane polymer containing one or more Si-H bonds per mer unit;
   (b) reacting said hydridosiloxane polymer with a hydroxyl-containing compound of the formula R'—OH, wherein R' is hydrogen, $C_1$-$C_{10}$ alkyl, or aryl of 1-2 rings, and may be substituted with hydroxyl, lower alkyl, lower alkoxy, halogeno, silyl, or amino groups, or combinations thereof, in an inert atmosphere in the presence of a catalyst effective to activate Si—H bonds, to provide a ceramic precursor in which hydrogen atoms in the hydridosiloxane polymer have been replaced by OR' moieties;
   (c) coating a substrate with said ceramic precursor; and
   (d) pyrolyzing said ceramic precursor on said substrate at a temperature of at least about 500° C. to provide a coating of said silicious ceramic material.

2. A method of preparing a coating of a silicious ceramic material on a substrate, which comprises:
   (a) providing a hydridosiloxane polymer containing one or more Si—H bonds per mer unit;
   (b) introducing carbon-containing moieties into said polymer by reaction with a compound containing an unsaturated carbon-carbon bond, in the presence of a catalyst effective to activate Si—H bonds, to give a ceramic precursor in which hydrogen atoms in the hydridosiloxane polymer have been replaced by carbon-containing moieties;
   (c) coating a substrate with said ceramic precursor; and
   (d) pyrolyzing said ceramic precursor on said substrate at a temperature of at least about 500° C. to provide a coating of said silicious ceramic material.

3. A method of preparing a coating of a silicious, nitrogen-containing ceramic material on a substrate, which comprises:
   (a) providing a hydridosiloxane polymer containing one or more Si—H bonds per mer unit;
   (b) introducing nitrogen-containing moieties into said polymer by reaction with a compound $NHR''_2$ wherein the R'' are independently selected from hydrogen, lower alkyl, sily, and aryl of 1-2 rings, in the presence of a catalyst effective to activate Si—H bonds, to give a ceramic precursor in which hydrogen atoms in the hydridosiloxane polymer have been replaced with nitrogen-containing moieties;
   (c) coating a substrate with said ceramic precursor; and
   (d) pyrolyzing said ceramic precursor on said substrate at a temperature of at least about 500° C. to provide a coating of said silicious, nitrogen-containing ceramic material.

4. A method of preparing a coating of a silicious, metal-containing ceramic material on a substrate, which comprises:
   (a) providing a hydridosiloxane polymer containing one or more Si—H bonds per mer unit;
   (b) reacting said hydridosiloxane polymer with a compound selected from the group consisting of $ML_a$ and M—OH, wherein M is a metal atom, L is an organic ligand associated therewith, and a represents the molar ratio L—M in said complex, in the presence of a catalyst effective to activate Si—H bonds, to provide a ceramic precursor in which said activated Si—H bonds have been replaced by Si—M bonds;
   (c) coating a substrate with said ceramic precursor; and
   (d) pyrolyzing said ceramic precursor on said substrate at a temperature of at least about 500° C. to provide a coating of said silicious, metal-containing ceramic material.

5. The method of claim 1, wherein said substrate is selected from the group consisting of metallic, glass, ceramic and graphite materials.

6. The method of claim 5, wherein said substrate is metallic.

7. The method of claim 5, wherein said substrate is glass.

8. The method of claim 5, wherein said substrate is ceramic.

9. The method of claim 5, wherein said substrate is graphite.

10. The method of claim 5, wherein said pyrolyzing is conducted at a heating rate between about 0.1° C. and 10.0° C. per minute.

11. The method of claim 5, wherein step (c) is carried out using flash pyrolysis.

12. The method of claim 2, wherein said substrate is selected from the group consisting of metallic, glass, ceramic and graphite materials.

13. The method of claim 12, wherein said substrate is metallic.

14. The method of claim 12, wherein said substrate is glass.

15. The method of claim 12, wherein said substrate is ceramic.

16. The method of claim 12, wherein said substrate is graphite.

17. The method of claim 12, wherein said pyrolyzing is conducted at a heating rate between about 0.120 C. and 10.0° C. per minute.

18. The method of claim 12, wherein step (c) is carried out using flash pyrolysis.

19. The method of claim 3, wherein said substrate is selected from the group consisting of metallic, glass, ceramic and graphite materials.

20. The method of claim 19, wherein said substrate is metallic.

21. The method of claim 19, wherein said substrate is glass.

22. The method of claim 19, wherein said substrate is ceramic.

23. The method of claim 19, wherein said substrate is graphite.

24. The method of claim 19, wherein said pyrolyzing is conducted at a heating rate between about 0.1° C. and 10.0° C. per minute.

25. The method of claim 19, wherein step (c) is carried out using flash pyrolysis.

26. The method of claim 4, wherein said substrate is selected from the group consisting of metallic, glass, ceramic and graphite materials.

27. The method of claim 26, wherein said substrate is metallic.

28. The method of claim 26, wherein said substrate is glass.

29. The method of claim 26, wherein said substrate is ceramic.

30. The method of claim 26, wherein said substrate is graphite.

31. The method of claim 26, wherein said pyrolyzing is conducted at a heating rate between about 0.1° C. and 10.0° C. per minute.

32. The method of claim 26, wherein step (c) is carried out using flash pyrolysis.

* * * * *